United States Patent [19]
Hayakawa et al.

[11] Patent Number: 5,265,614
[45] Date of Patent: Nov. 30, 1993

[54] ACOUSTIC COUPLER

[75] Inventors: Kenichi Hayakawa, Kawasaki; Kenji Kawabe, Yokohama; Kazuhiro Watanabe, Tokyo; Kiyoto Matsui, Kawasaki; Takaki Shimura, Machida; Shiro Takeda, Sagamihara, all of Japan

[73] Assignee: Fujitsu Limited, Kawasaki, Japan

[21] Appl. No.: 427,127

[22] PCT Filed: Aug. 29, 1989

[86] PCT No.: PCT/JP89/00881
§ 371 Date: Oct. 12, 1989
§ 102(e) Date: Oct. 12, 1989

[87] PCT Pub. No.: WO90/01902
PCT Pub. Date: Mar. 8, 1990

[30] Foreign Application Priority Data
Aug. 30, 1988 [JP] Japan .................. 63-215702
Aug. 30, 1988 [JP] Japan .................. 63-215703

[51] Int. Cl.$^5$ ............................... A61B 8/00
[52] U.S. Cl. ................... 128/602.03; 128/663.01
[58] Field of Search ............ 128/662.03–662.06

[56] References Cited
U.S. PATENT DOCUMENTS

| | | | |
|---|---|---|---|
| 4,408,692 | 10/1983 | Sigel et al. | 206/438 |
| 4,608,989 | 9/1986 | Drue | 128/662.03 X |
| 4,688,578 | 8/1987 | Takano et al. | 128/662.03 |
| 4,867,169 | 9/1989 | Machida et al. | 128/662.03 |
| 4,901,729 | 2/1990 | Saitoh et al. | 128/662.03 |
| 5,070,881 | 12/1991 | Weiland | 128/662.03 |
| 5,078,149 | 1/1992 | Katsumoto et al. | 128/662.03 |

FOREIGN PATENT DOCUMENTS

| | | |
|---|---|---|
| 0059785 | 9/1982 | European Pat. Off. . |
| 0211482 | 2/1987 | European Pat. Off. . |
| 8633958 | 7/1987 | Fed. Rep. of Germany . |
| 3722942 | 2/1988 | Fed. Rep. of Germany . |
| 59-11708 | 1/1984 | Japan . |
| 59-49750 | 3/1984 | Japan . |
| 59-82838 | 5/1984 | Japan . |
| 61-288842 | 12/1986 | Japan . |
| 63-36173 | 2/1988 | Japan . |
| 63-49146 | 3/1988 | Japan . |
| 2036504 | 6/1990 | United Kingdom . |

OTHER PUBLICATIONS

International Search Report for International Application No. PCT/JP89/00881, European Patent Office, Nov. 22, 1989.

*Primary Examiner*—Francis Jaworski
*Attorney, Agent, or Firm*—Staas & Halsey

[57] ABSTRACT

An acoustic coupler, combined with an ultrasound probe, is made of a gel a part of which is hardened for providing holding means for holding the probe for lifting up the probe with the coupler and another part of which is used to form an acoustically transparent path between the probe and a surface of an object to be acoustically inspected. Poly vinyl alcohol (PVA) is a typical material for the gel, and the coupler is fabricated by molding a PVA solution by partially increasing concentration of PVA and/or a repeating frequency of refrigerating and thawing the PVA solution, compared with those for the transparent path, in a molding process of the coupler.

19 Claims, 14 Drawing Sheets

ENLARGED VIEW OF A

ACOUSTIC COUPLER

BACKGROUND OF THE INVENTION a. Field of the Invention

The present invention relates to an acoustic coupler provided between an ultrasound probe and a surface of a body to be diagnosed.

b. Description of the Related Art

An ultrasound probe including an ultrasonic transducer is used for diagnosing an affected part in a human body by holding the probe to a surface of the human body. During holding the probe to the body, the ultrasonic transducer transmits an ultrasonic wave which is formed into an ultrasonic beam for scanning the body, and receives ultrasonic echoes from the body along the beam.

As well known, the ultrasonic transducer has two types, a single type having a single ultrasonic transducer and an array type having plural ultrasonic transducers arranged either in a line an in a matrix. Therefore, the size and shape of the ultrasound probe is varied in accordance with the type of the ultrasonic transducer.

When the surface of the body is soft so that the ultrasound probe can be tightly fitted to the surface of the body and when the affected part is located from the surface of the body as deeply as the ultrasonic echoes can be focused well with a sufficient depth of field, the probe can be used in a state being directly held to the surface of the body through a thin layer of water, vegetable, oil, glycerin or liquid paraffin. The thin layer prevents multi-reflection caused by an air gap between the probe and the surface of the body.

On the other hand, when the surface of the body is not soft or not flat to the ultrasound probe as in a case that the thyroid gland or the carotid artery is diagnosed by the ultrasound probe, it is hard to hold the probe to the surface of the throat tightly without leaving the air gap. Furthermore, when the affected part is located near the surface of the body as in a case of diagnosing the thyroid gland, carotid artery or mamma cancer, it is hard to detect ultrasonic echoes from the affected part with sharp resolution, because the echoes are focused within a thin depth of field. In these cases, an acoustic coupler having a thickness of approximately 1 to 10 cm is used between the ultrasound probe and the surface of the body. The thickness of the acoustic coupler is varied in accordance with the flatness of the surface of the body and/or the location of the affected part from the surface of the body.

The material of the acoustic coupler must have low acoustic attenuation and acoustic impedance required to be equal to the surface of the human body. This kind of material will be called an "acoustically transparent material" or simply a "transparent material" hereinafter. As the transparent material for the acoustic coupler, water put in a bag has been used, using a transparent elastic material such as silicon rubber for the bag. Water is easily obtained and can be used in a hygienic condition so there is no worry of making the body dirty. However, there were problems that the bag would have been broken, resulting in splashing water on the body. This problem has been solved by using a gelled material for the acoustic coupler. A gelled material can be made so as to be acoustically transparent. Further, it is easy to apply to the surface of the body without leaving an air gap, and it is easy to remove from the surface, leaving no fragment of the gel material. Such gelled material will be simply called a "gel" hereinafter.

In regard to the gel and its application to the acoustic coupler, there have been many patents (Japanese laid opened patents). For instance: SHO 59-11708 to IMAI on Jan. 25, 1984 discloses a gel applicable to the acoustic coupler, such as a silicon rubber gel, a water gel, an oil gel or a gel mixed with water and oil; SHO 59-49750 to MIYAMOTO et al. on Mar. 22, 1984 discloses a gel called a poly vinyl alcohol (PVA) gel which a kind of a hydrated gel containing approximate 80% of water content, having large elasticity and hardness and very small acoustic attenuation. The elasticity and the hardness depend on a refrigerating temperature and a frequency of repeating refrigeration-and-thaw of a PVA material, performed in a fabricating process of the PVA gel; SHO 59-82838 to MIYAMOTO et al. on May 14, 1984 discloses the details of the PVA gel, for instance, about composition, relation between water content and acoustic attenuation and between water content and hardness of the PVA gel, and the patent explains that the PVA gel can be plastically formed so as to be fitted to the ultrasound probe when the PVA gel is hardened properly; SHO 61-288842 by FURUTA et al. on Dec. 19, 1986 discloses a probe applicator the same as the acoustic coupler, consisting of a U shaped case adaptable to the ultrasound probe and water or some kind of gel put in the U shaped case; SHO 63-36173 by MACHIDA et al. on Feb. 16, 1988 discloses an acoustic coupler mountable on an ultrasound probe, consisting of a case having a tapered shape so that one end of the case to be fitted to the probe is large and the other end of the case to be put on the surface of the body is small and water or a colloidal solid put in the tapered case; and SHO 63-49146 by MACHIDA Mar. 1, 1988 discloses an acoustic coupler consisting of a case having different portions for mounting the ultrasound probe water put in a bag or a colloidal material put in a bag installed in the case, wherein the different mounting portions are for mounting the ultrasound probe in different directions toward the surface of the body. This is caused by the fact that the probe is often required to be oriented to the surface of the body in at least two directions, a perpendicular direction to the surface of the body and a parallel direction to the surface of the body, the latter being required in such a case that blood in a blood vessel running near the surface parallel to the surface of the body is to be diagnosed by ultrasonic waves.

Some of the above-mentioned patents disclose acoustic couplers each including a case having a membrane, to which the surface of the body is applied, and a gel or a colloidal material filled in a gap between the case and the membrane. However, in this case, there is a problem that the ultrasonic waves (the ultrasonic echoes) are attenuated by the membrane. The attenuation is caused by an acoustic attenuation of the membrane of course, mainly caused by multi-reflection due to the different acoustic impedance between the body and the membrane.

Generally, a gel is a material which is difficult to be mechanically caught or held by a small supporting area because of its lack of hardness and viscosity. Therefore, the gel is often used in a state of being simply laid on the surface of the body without putting the membrane between the surface and the gel, and the ultrasound probe is applied on the laid gel. However, this is inconvenient for one (an operator) operating the ultrasound probe, because the operator always must contact the gel with both hands independently of treating the ultrasound probe. As a result, the gel has been used inevitably by putting it in a case having a membrane even though multi-reflection occurs due to the membrane.

However, in the above-mentioned, SHO 59-49750 and SHO 59-82838 by MIYAMOT et al. teach, respectively about the acoustic coupler made of the PVA gel. In particular, SHO 59-82838 teaches a concept that the PVA gel can be fitted to the ultrasound probe by hardening the PVA gel properly. This is important because SHO 59-82838 suggests that the PVA gel can be used as an acoustic coupler when directly combined with the ultrasound probe without using the case and the membrane. However, SHO 59-82838 teaches nothing about the structure of an acoustic coupler using the hardened PVA gel.

Irrespective of a general gel or a PVA gel, an acoustically transparent gelled material is difficult to be applied to an acoustic coupler unless a case and a membrane are used in the acoustic coupler. Since, as stated before, the gelled material has small hardness and viscosity, it has been a difficult problem to overcome.

SUMMARY OF THE INVENTION

An object (a first object) of the present invention is to provide an acoustic coupler having a gelled material capable of being easily combined with an ultrasound probe and directly applied to the surface of the body.

Another object (a second object) of the present invention is to provide a method of fabricating an acoustic coupler having a gelled material capable of being easily combined with an ultrasound probe and directly applied to the surface of the body.

Still another object (a third object) of the present invention is to provide an acoustic coupler having a gelled material capable of being easily combined with an body in which it is easy to change a direction of the ultrasound probe combined with the gelled matural with respect the surface of the body.

Yet another object (a fourth object) of the present invention is to provide a container for stocking an acoustic coupler having a gelled material capable of being easily combined with an ultrasound probe and directly applied to the surface of the body, in a state ready for combining with an ultrasound probe by one touch at any time required.

The first object is achieved by applying, to the acoustic coupler, an acoustically transparent general gelled material such as a silicon gel or a paraffin gel, which will be called simply a "general gelled material" hereinafter, and a combiner made of an elastic material such as silicon rubber, for combining the general gelled material with the ultrasound probe. A part at one side of the combiner is buried in the general gelled material and another part at an opposite side of the combiner is freely, opened for accepting the probe. When the probe is pushed into the opened combiner, the combiner catches an end part of the probe tightly, using the elastic force of the combiner. An upper side of the general gelled material is fitted to the end of the probe and a lower side is formed to a face directly applied to the surface of the body.

The first object is also achieved by applying another kind of gelled material such as a PVA gel to the acoustic coupler. In this case, a combiner is not necessary. Instead of that, an inlet mechanism made by hardening a part of the PVA gel is used for catching the end part of the ultrasound probe, using the elastic force of the hardened part. An upper side of the PVA gel is fitted to the end of the probe and a lower side is formed to a face directly applied to the surface of the body.

The second object of fabricating the acoustic coupler using the general gelled material is achieved by making a part at one side of the combiner so as to have a structure by which the combiner is tightly and mechanically connected with the general gelled material.

The second object of fabricating the acoustic coupler using the PVA gel is achieved by increasing the hardness of the PVA gel around the inlet structure by partially increasing the concentration, polymerization degree and/or the degree of hydrolysis of the PVA gel and/or partially repeating the refrigerating process.

The third object is achieved by applying a relatively large amount of the general gelled material or the PVA gel with a combiner made of an elastic material such as a silicon rubber. An upper surface of the general gelled material or the PVA gel is fitted to the end of the ultrasound probe and the combiner is provided around the upper surface, and a lower surface of the gel is formed to a glove-shaped bottom surface to which is applied to the surface of the body. The direction of an ultrasonic wave from the probe combined with the general gelled material or the PVA gel can be changed in any direction to the surface of the body by turning the probe along the glove-shaped bottom surface.

The fourth object is achieved by providing a container for stocking the acoustic coupler in a liquid, such as water, for preserving the coupler from being dried up. Around a mouth of the container for putting water and the coupler in the container and for inserting the end part of the ultrasound probe into the container, there is structure for making the combining structure of the coupler ready to easily accept the probe when the coupler is put in the container. At the same place around the mouth, there is other structure for making the combining structure of the coupler catch the end part of the probe when the probe is inserted in the container and the end of the probe is fitted to the coupler, so that the probe can be pulled up from the container with the coupler without touching the coupler by hand.

DESCRIPTION OF THE PREFERRED EMBODIMENTS

Before disclosing the preferred embodiments for carrying out the present invention, a reason for using an ultrasound probe in combination with an acoustic coupler will be explained in reference to FIGS. 1(a) and 1(b), and a prior art acoustic coupler combined with an ultrasound coupler will be explained in reference to FIGS. 2(a) and 2(b).

Figure 1:
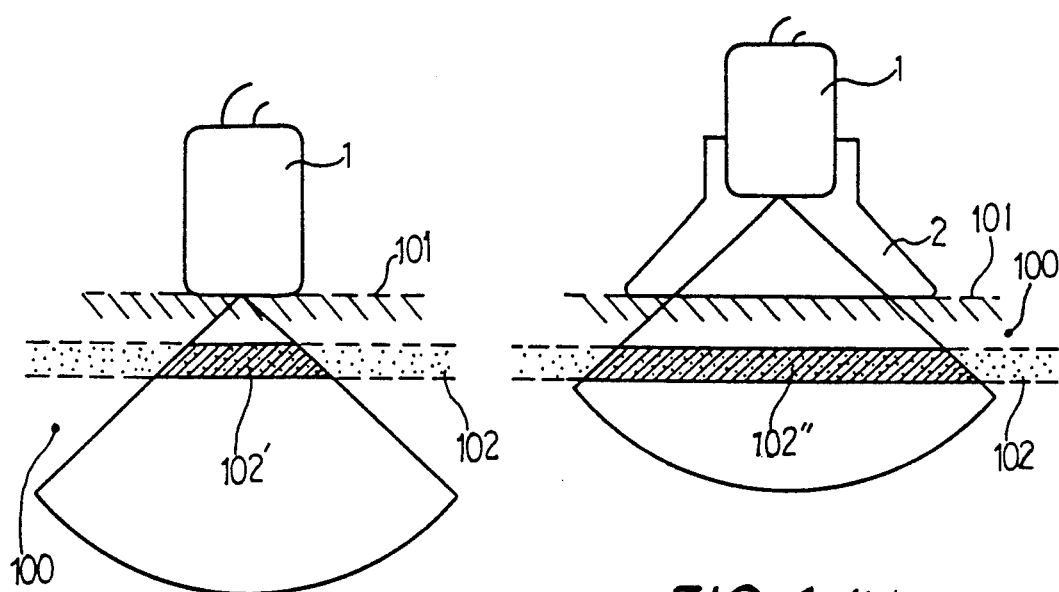
FIG. 1(a) is a schematic cross-sectional view illustrating an ultrasound probe directly applied to a surface of a body for acoustically diagnosing the body.
FIG. 1(b) is a schematic cross-sectional view illustrating the ultrasound probe applied to the surface of the body through an acoustic coupler.
Figure 2:
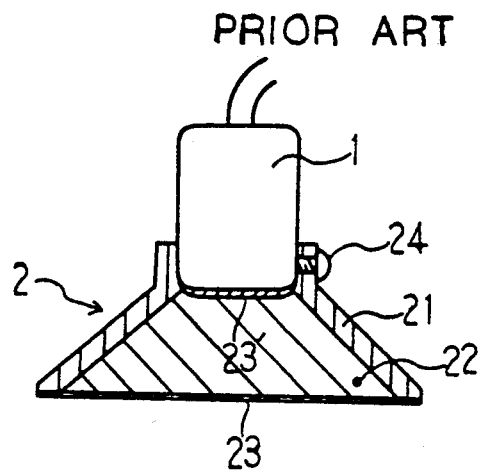
FIG. 2(a) is a schematic cross-sectional view illustrating an acoustic coupler of the prior art, combined with an ultrasound probe.
FIG. 2(b) is a schematic perspective view of a prior art case for the acoustic coupler in FIG. 2(a)
Figure 2:
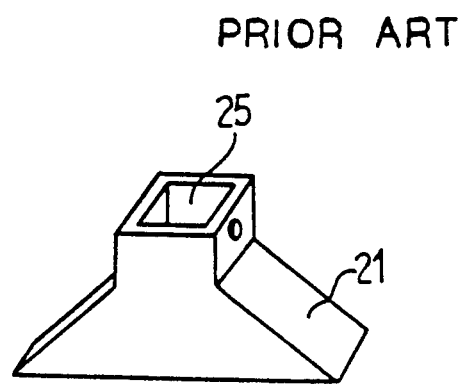

FIG. 1(a) illustrates an ultrasound probe 1 directly applied to a surface 101 of a human body 100 for diagnosing a blood vessel 102 running near the surface 101. Actually, a transparent thin layer is applied to the surface 101 but not depicted in FIG. 1(a); When an ultrasonic wave is transmitted from the ultrasound probe 1, forming a field view 1—1 as shown in FIG. 1(a), only a small part, shown by a hatched part 102′, of the blood vessel 102 is observed. In addition, it is difficult to focus ultrasonic echoes from the blood vessel 102 because of the small depth of the field. These problems are solved by inserting an acoustic coupler 2 between the probe 1 and the surface 101 as shown in FIG. 1(b). By inserting the acoustic coupler 2, the blood vessel 102 can be observed in a wide range as shown by a hatched a part 102″ in FIG. 1(b) and the ultrasonic echoes can also be made to focus properly.

In the prior art, the acoustic coupler 2 consists of a case 21, transparent membranes 23 and 23′ and a transparent material 22 filled in the space formed by the case 21 and the membranes 23 and 23′, as shown in FIG. 2(a). As the transparent material 22, water has been used. However, recently, a transparent gelled material has been used. However, the ultrasonic wave and the ultrasonic echoes are attenuated by the membranes 23′; further and there has been inconvenience because the acoustic coupler 2 must be combined with the ultrasound probe I by fixing the case 21 by some means, for instance, with a screw 24 every time the coupler 2 is changed. These are troublesome problems associated with prior art, case 21 has an inlet mechanism 25, as shown in a perspective view of the case 21 of FIG. 2(b), for combining the acoustic coupler 2 with an end part of the ultrasound probe 1.

Figure 3:
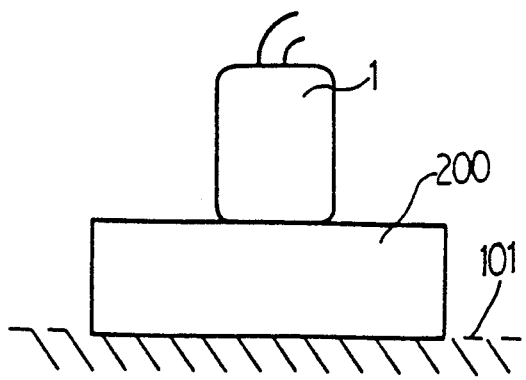
FIG. 3(a) is a schematic view for illustrating a block of an acoustically transparent gelled material applied between an ultrasound probe and a surface of a body.
FIG. 3(b) is a schematic perspective view of the block in FIG. 3(a)
Figure 3:
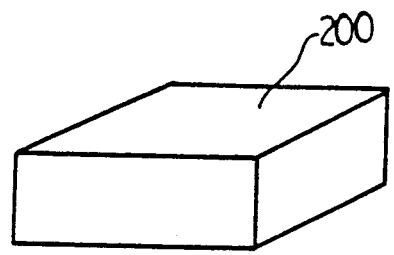

Since the transparent gelled material has little although some hardness and viscosity, the gelled material can be formed to a block as shown by a reference numeral 200 in FIG. 3(b) and can be used as an acoustic coupler capable of freely putting it on the surface 101 as shown in FIG. 3(a). In some cases, such a block is useful, however in most cases, the block is inconvenient to use because the block must be moved independently of the ultrasonic probe, always using both hands.

These problems in the prior art are solved by combining the gelled material and the ultrasound probe without using the case and the membrane. This is achieved by the present invention as will be disclosed in the following embodiments.

In the embodiments of the present invention, an acoustically transparent gelled material is separate into two categories, one of which includes a material having properties that its hardness is difficult to be partially changed and the other of which includes a material having properties that its hardness, therefor, elasticity is easy to be partially changed. The former is a well known material such as a silicon gel or paraffin gel and called a "general gelled material" as stated before, and the latter is a material such as the PVA gelled material, called the "PVA gel" hereinafter. The properties of the PVA gels used in the present invention are as follows:

PVA gel having a large or high hardness

Polymerization degree: 1700
A degree of hydrolysis: 99.5 mol %
Concentration of PVA: 20 wt %
Hardness (elastic modulus): $2 \times 10^3 N/m^2$ (PVA gel having a small or low hardness)

Polymerization degree: 1700
A degree of hydrolysis: 99.5 mol %
Concentration of PVA: 10 wt %
Hardness (elastic modulus): $4 \times 10^2 N/m^2$
Acoustic impedance: $1.58 \times 10^6$ $(kg/m^2)s$
Acoustic attenuation: 0.07 dB/cm/MHz.

Figure 4:
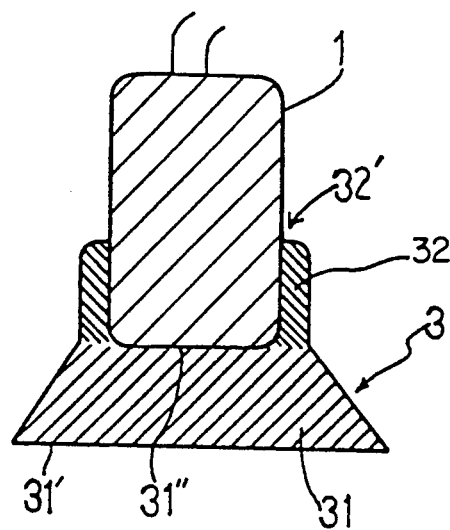
FIG. 4 is a schematic cross-sectional view of an acoustic coupler embodying the present invention, made of an acoustically transparent PVA gelled material, combined with an ultrasound probe.

FIG. 4 illustrates a cross sectional view showing an acoustic coupler 3 made of only the PVA gel and combined with the ultrasound probe 1. In FIG. 4, the same reference numeral as in FIG. 2 designates the same unit as in FIG. 2. In FIG. 4, the coupler 3 is depicted in two parts, a part 31 and a part 32. However materials composing parts 31 and 32 are same, only their hardness is different. That is, the hardness of the part 32 is larger or greater than that of the part 31, however acoustical transparency of the part 31 is greater than that of the part 32. Because of hardening of the part 32, the coupler 3 can be combined tightly with the probe 1 using the elastic force of the part 32. The probe 1 can be slide in an inlet mechanism (a round hole) 32' made by the hardened PVA gel (the part 32). When using the probe 1 with the coupler 3, a lower surface 31' of the coupler 3 is directly applied to the surface of the body and an upper surface 31" of the coupler is fitted to an end of the probe 1, and the ultrasonic waves and the ultrasonic echoes are passed through the part 31.

Figure 5:
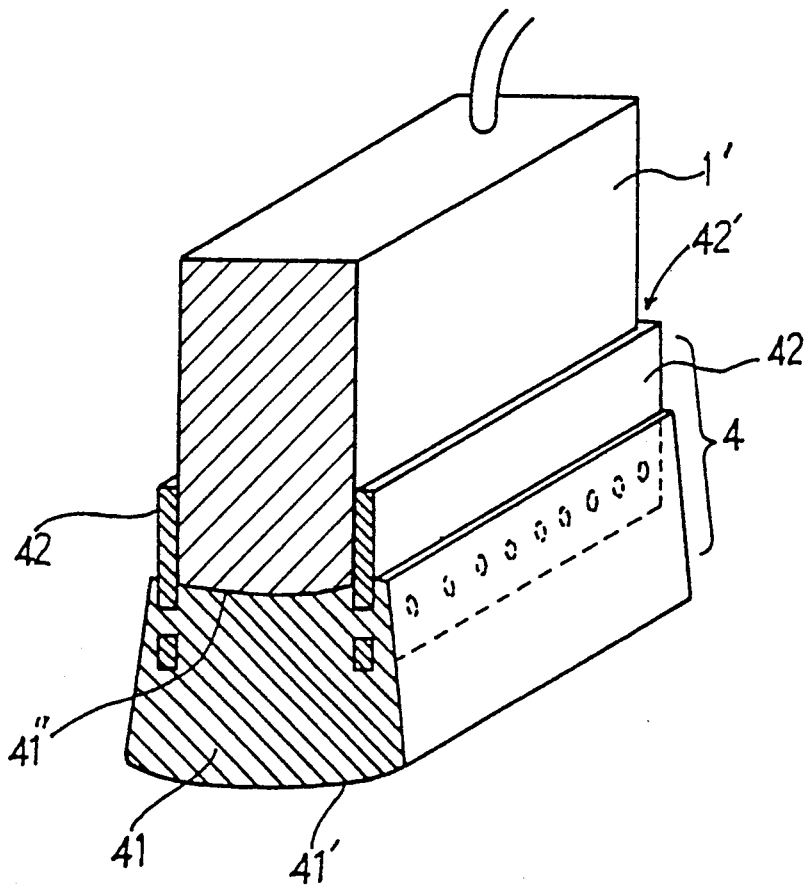
FIG. 5 is a schematic perspective view of an acoustic coupler embodying the present invention, made of an acoustically transparent general gelled material or PVA gel and having a combiner, combined with an ultrasound probe including a linear array transducer.

FIG. 5 illustrates a perspective view and partially cross sectional view of an acoustic coupler 4 combined with an ultrasound probe 11 including an array type transducer not depicted. In this case, the ultrasound probe 1' is relatively large in size, so that the acoustic coupler 4 is large in size and heavy in weight. Therefore, a combiner 42 made of elastic material such as silicon rubber is necessary, and a gelled material 41 is used as shown in FIG. 5. Either the general gelled material or the PVA gel not partially hardened can be used as the gelled material 41. The combiner 42 is formed like a stand-up collar whose upper side forms an inlet mechanism 42' (a square hole) into which the probe 1' is pushed until an end surface of the probe 1' is fitted to an upper surface 41" of the gelled material 41. The stand-up collar of the combiner 42 catches the end part of the probe 1' tightly by the elastic force mainly of the combiner 42 but also of the gelled material 41. A embeded side of the stand-up collar of the combiner 42 is buried 41. A plurality of holes are provided in the gelled material at the embedded side for increasing the force connecting the combiner 42 and the gelled material 41. Usually, the holes, each having 2 mm diameter, arranged in 4 mm, pitch are enough for an acoustic coupler for a typical array type ultrasound probe. A lower surface 41' of the gelled material 41 is directly applied to the surface of the body.

Figure 6:
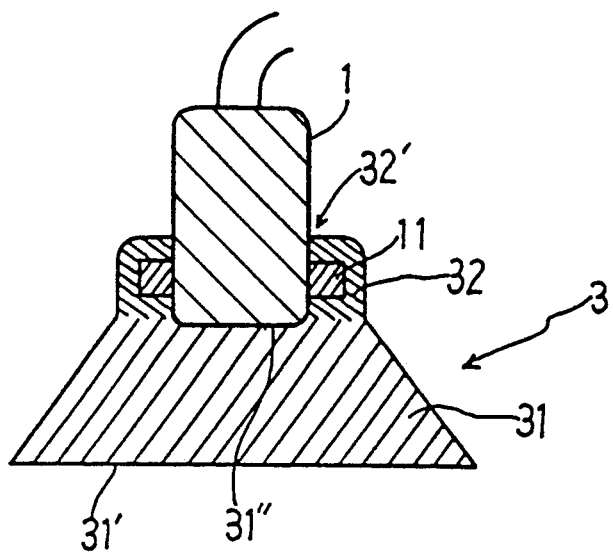
FIG. 6 is a schematic cross-sectional view illustrating an acoustic coupler of PVA gel, combined with an ultrasound probe, using a ring fitted to the probe.

FIG. 6 shows an illustration of an acoustic coupler similar to that shown in FIG. 4. In FIG. 6, the same reference numerals designate the same unit or part as in FIG. 4. The difference between the cases of FIGS. 6 and 4 is that in the case of FIG. 6, a ring 11 is fitted at the end part of the probe 1 and a round ditch or groove be be fitted to the protruded ring 11 is provided inside of the inlet mechanism 32'. The reason for providing the ring 11 is that the coupler 3 has a large size, and therefore, has a heavy weight. That is by providing the ring 11 to the probe 1, the friction between the probe 1 and the coupler 3 increases, so that the probe 1 can be lifted up together coupler 3. The coupler 3 is combined with the probe 1 by opening the inlet mechanism 32' against the elastic force of the part 32 and pushing the end part of the probe 1 into the opened inlet mechanism 32'. The ring 11 is made by a solid material having friction against the hardened PVA gel, such as silicon rubber or nature rubber and fitted to the probe 1. The ring can be removed from the probe 1.

Figures 7A, 7B:
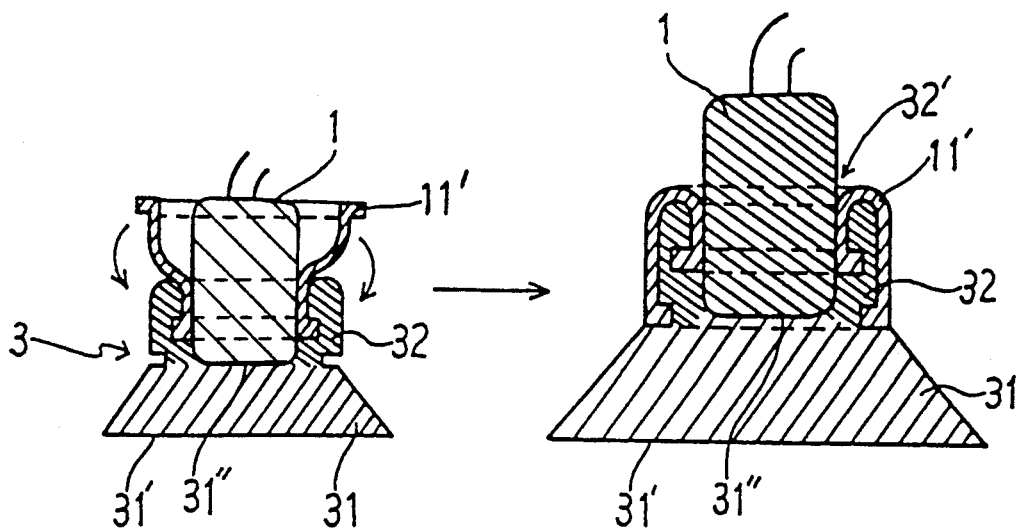
FIGS. 7(a) and (b) are schematic cross-sectional views each illustrating an acoustic coupler of PVA gel, combined with an ultrasound probe, using a headband type holder on the probe.

If the weight of the coupler is really heavy, compared with the weight of the coupler shown in FIG. 6, an elastic probe combiner 11' can be attached to the end part of the probe 1 as shown in FIGS. 7(a) and 7(b). In FIGS. 7(a) and 7(b), the same reference numerals as in FIG. 6 designate the same unit or part. The elastic probe combiner 11' is made of an elastic material such as silicon rubber or nature rubber and formed like a headband surrounding the end part of the probe 1. The part 32 of the hardened PVA gel is also formed so as to fit the closed elastic probe combiner 11' as shown in FIG. 7(b). When the probe 1 is combined with the coupler 3, the end part of the probe 1 is inserted into the inlet mechanism 32', with the combiner open as shown in FIG. 7(a), until the end of the probe 1 is fitted to the upper surface 31" of the PVA gel 31 of the coupler 3. After the end of the probe 1 is fitted to the upper surface 31', the coupler is combined with the probe 1 by closing the probe combiner 11' so as to cover the part 32 as shown in FIG. 7(b).

Figure 8:
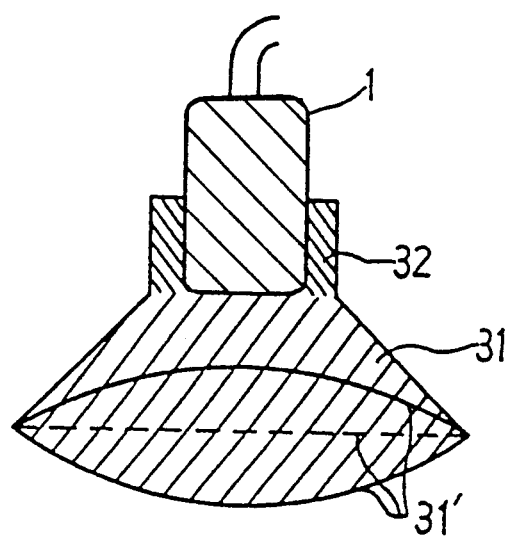
FIG. 8 is a schematic cross-sectional view illustrating that a lower surface of an acoustic coupler made of the gelled material can be changed in shape.

The lower surface 31' of the PVA illustrated in FIGS. 4, 6 or 7(b) is formed to a flat surface. However, the surface 31' can be varied to any form so as to fit to the surface of the body, for instance, to a concave or convex surface as shown in FIG. 8. In FIG. 8, the same reference numerals as in FIG. 6 designate the same unit or part. The bottom surface, to which the surface of the body is applied, of the acoustic coupler can be also varied in the case of FIG. 5.

Figure 9A:
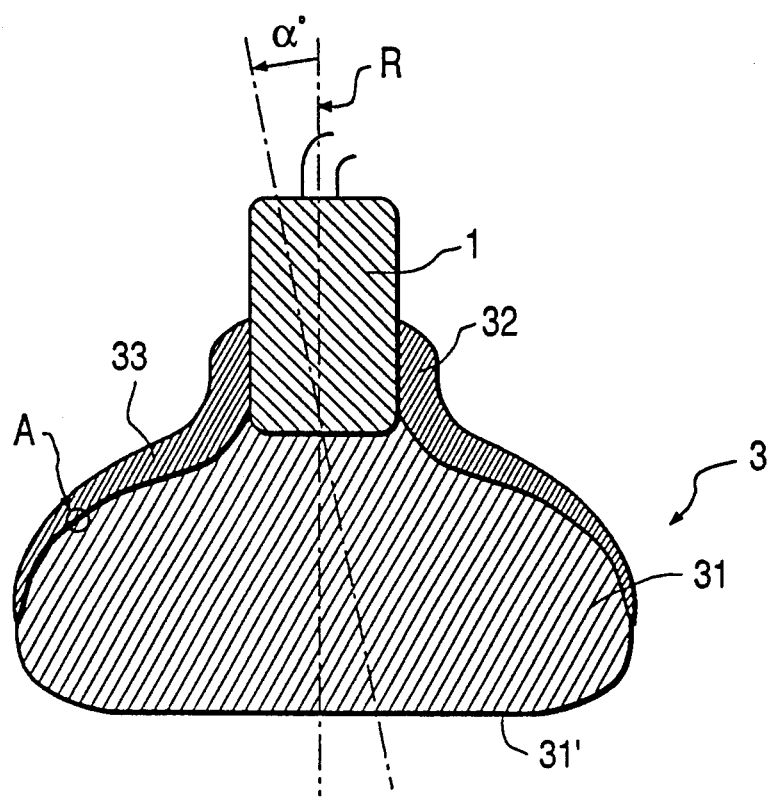
FIG. 9(a) is a schematic cross-sectional view illustrating an acoustic coupler made of the gelled material which is combined with an ultrasound probe and provided with a case.
Figure 9B:
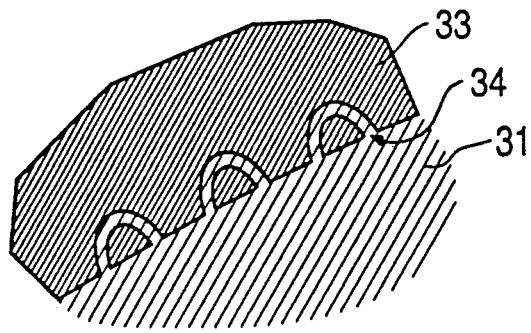
FIG. 9(b) is an enlarged view at reference symbol A in FIG. 9(a)

In ultrasonic diagnosing, the a direction of the ultrasound probe to the surface of the body is often required to be changed. For instance, where measuring the speed of blood flowing through a blood vessel running near the surface of the body parallel to the surface, the probe must be laid against the surface of the body so as to detect the blood flowing through the blood vessel. FIG. 9(a) shows a case capable of laying an ultrasound probe on the surface of the body by using the elastic characteristic of the gelled material. In FIG. 9(a) an ultrasound probe 1 is combined with an acoustic coupler 3 using PVA gel 31 very large in size for allowing the probe 1 to incline ($\alpha°$) from a vertical line R. In FIG. 9(a) and 9(b), the same reference numeral as used in FIG. 4 designate the same unit or part. In FIG. 9(a) a case 33 is newly provided to the coupler 3. Since the weight of coupler 3 is very heavy, the probe 1 cannot be lifted up with the coupler 3 if the coupler 3 is combined with the probe 1 by the inlet mechanism made by a hardened PVA gel as done in FIG. 4. The case 33 is made of an elastic material such as silicon rubber and has structure that an upper part, holding the probe 1, of the case 33 is thicker than a part, near to the bottom surface 31', of the case 33. This is for making the case 33 flexible because the PVA gel 31, connected with the case 33, changes its form as the probe 1 is inclined. Furthermore, the case 33 has a mechanism for mechanically connecting the case 33 tightly with the PVA gel 31 as shown in FIGS. 9(a) and 9(b). FIG. 9(b) is an enlarged of reference symbol A in FIG. 9(a). FIG. 9(b), shows that there are many small holes 34 to be filled up by the PVA gel 31 at the inside of the case 33.

Figure 17:
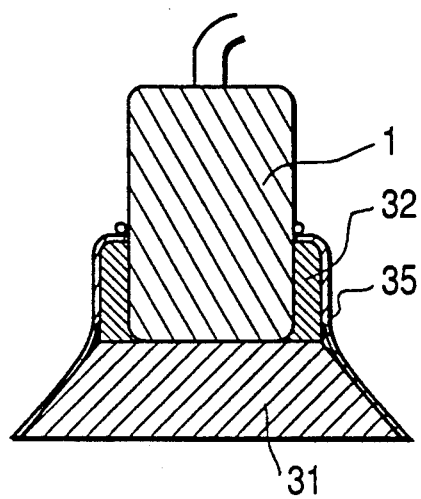
FIG. 17 is a schematic cross-sectional view illustrating a cover put on an acoustic coupler.
Figure 18:
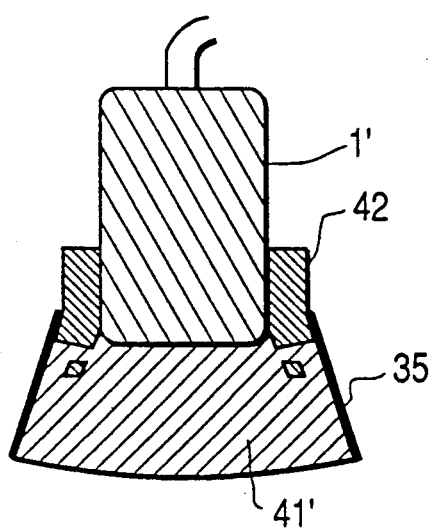
FIG. 18 is a schematic cross-sectional view illustrating another cover put on another acoustic coupler.

The water content of the gelled material is usually more than 80%, so that the water in the gelled material intends to evaporate to the air, resulting in increasing acoustic attenuation. Therefore, when the acoustic coupler using the gelled material is use for a relatively long time, the gelled material should be covered by a proper film 35 such as a sheet of silicon rubber, vinyl or polyethylene, as shown in FIGS. 17 and 18. In FIG. 17, the same reference numerals as used in FIG. 4 designate the same unit or part and in FIG. 18, the same reference numerals as used in FIG. 5 designate the same unit or part.

A method of fabricating the acoustic coupler, made of the PVA gel partially hardened for combining the ultrasound probe as explained in FIGS. 4, 6 or 7, will be disclosed. There are three methods, namely first, second and third methods, which will be disclosed with reference to FIGS. 10(a-e), 11(a-f) and 12(a-f) respectively.

Figure 10A:
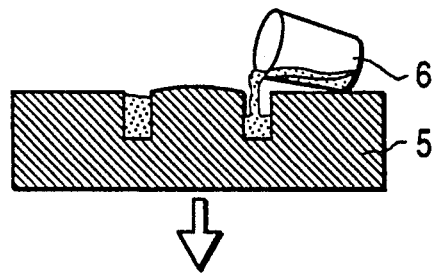
FIGS. 10(a) through (e) are schematic cross-sectional views illustrating steps of a method for fabricating an acoustic coupler made of the PVA gel.
Figure 10B:
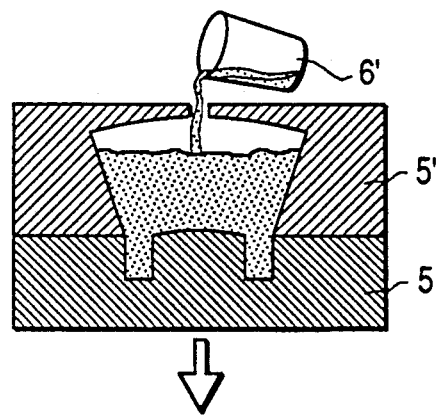
Figure 10C:
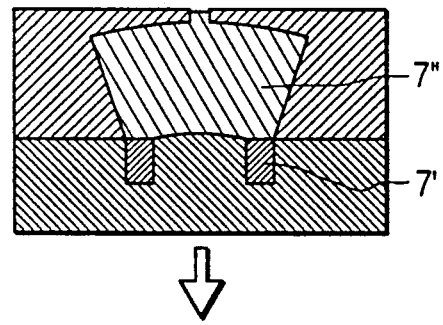
Figure 10D:
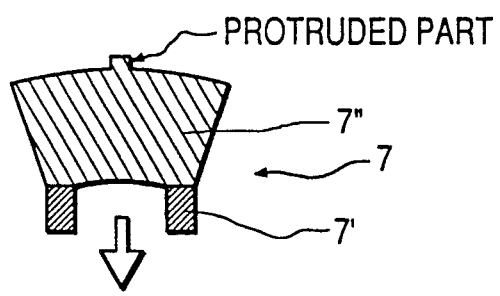
Figure 10E:
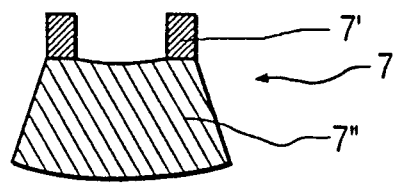

The first method is performed by the following steps with reference to FIGS. 10(a-e):

(1) providing a box 5 for molding a hardened PVA gel, pouring an aqueous solution 6 of 20% wt (more than 20% wt can be taken) PVA into the box 5 as shown in FIG. 10(a) and leaving the solution 6 in the box 5 at a room temperature;

(2) putting a box 5' for molding a usual PVA (not hardened) gel on the box 5 and pouring an aqueous solution 6' of 10 wt % (less than 10 wt % can be taken) PVA into the box 5' as shown in FIG. 10(b);

(3) repeating cycle of refrigerating, to less than −20° C., and thawing, to a room temperature, the solutions 6 and 6' in the boxes 5 and 5', respectively, twice (more than once can be taken) so that the solutions 6 and 6' become gels 7' and 7" respectively and are connected each other as shown in FIG. 10(c); and (4) taking out a PVA gelled material 7 formed to an ultrasonic coupler, from the boxes 5 and 5' as shown in FIG. 10(d), and cutting off a protruded part produced in molding, as shown in FIG. 10(e).

The typical dimensions and properties of the acoustic coupler fabricated by the above process are as follows:

couplers' dimensions

Width: 30 mm
Height: 50 mm
Depth: 100 mm
Inlet structure thickness: 5 mm hardened PVA gel Polymerization degree: 1700
A degree of 99.5 mol %
Concentration of PVA: 20 wt %
Hardness(elastic modulus): $2 \times 10^3 N/m^2$ (PVA gel having small or low hardness Polymerization degree: 1700
A degree of hydrolysis: 99.5 mol %
Concentration of PVA: 10 wt %
Hardness(elastic modulus): $4 \times 10^2 N/M^2$
Acoustic impedance: $1.58 \times 10^6 kg/(m^2 s)$
Acoustic attenuation: 0.07 dB/cm/MHz.

Figure 11A:
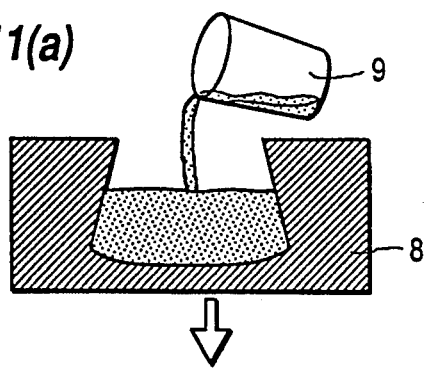
FIGS. 11(a) through (f) are schematic cross-sectional views illustrating steps of another method for fabricating an acoustic coupler made of the PVA gel.
Figure 11E:
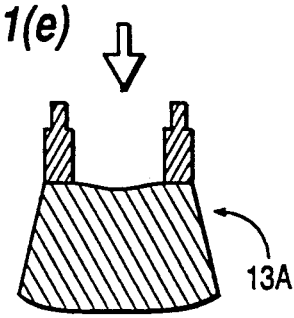
Figure 11B:
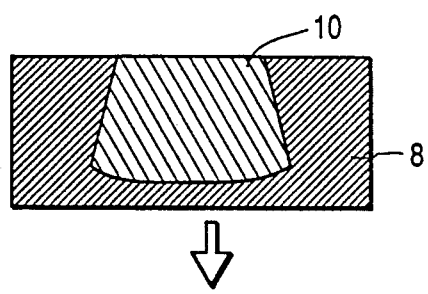
Figure 11F:
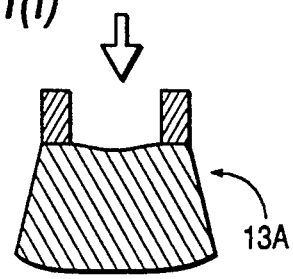
Figure 11C:
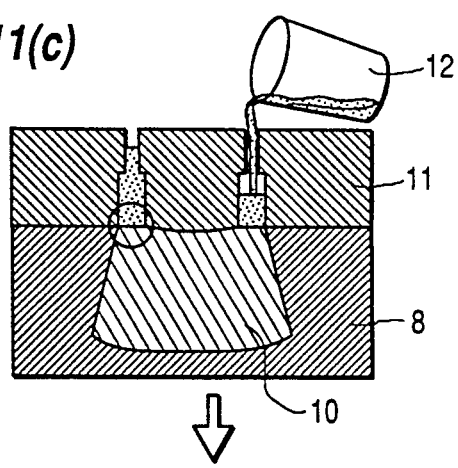
Figure 11C:
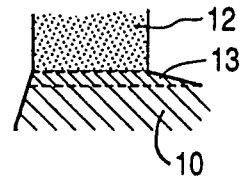
Figure 11D:
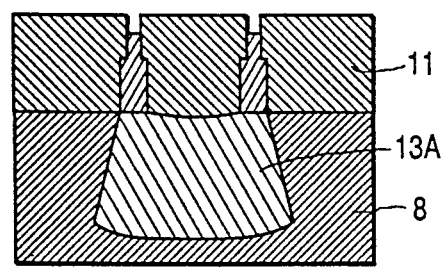

The second method is performed by the following steps with reference to FIGS. 11(a-f):

(1) pouring an aqueous solution 9 of 10% wt (less than 10% wt can be taken) PVA into a box 8 for molding the usual PVA gel as shown in FIG. 11(a);

(2) gelling the aqueous solution 9 in the box 8 to a usual PVA gel 10 by refrigerating the aqueous solution 9 in the box 8 to −20° C. (less than −20° C. can be allowed) and thawing that to a room temperature as shown in FIG. 11(b);

(3) putting a box 11 for molding the hardened PVA gel on the box 8, and pouring an aqueous solution 12 of 20% wt (more than 20% wt can be taken) PVA and heated up to 90° C. (more than 80° C. is allowable) into the box 11 as shown in FIG. 11(c), which results in partially melting the usual PVA gel 10 near the interface between the usual PVA gel 10 and the poured hot solution 12 as shown by reference numeral 13 in FIG. 11(c');

(4) refrigerating the poured solution 12 and the usual PVA gel 10° to −20° C. (less than −10+ C. is allowable) and thawing them to a room temperature, which results in gelling them to a gelled material 13A of a hardened PVA gel and a usual PVA gel connected each other as shown in FIG. 11(d); and (5) taken the the gelled materially 13A out from the boxes 11 and 8 as shown in FIG. 11(e), and cutting out protruded parts as shown in FIG. 11(f).

Figure 12A:
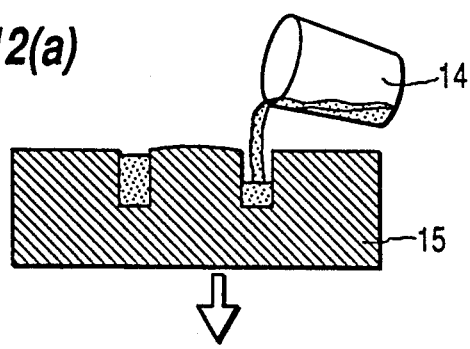
FIGS. 12(a) through (f) are schematic cross-sectional views illustrating steps of still another method for fabricating an acoustic coupler made of the PVA gel.
Figure 12E:
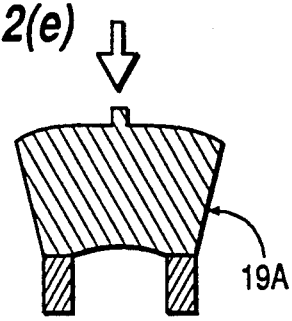
Figure 12B:
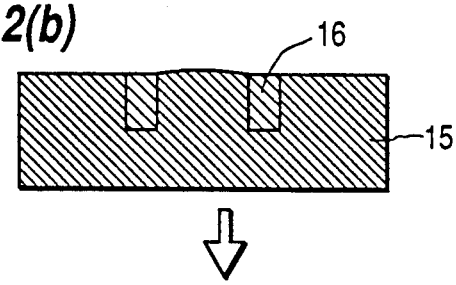
Figure 12F:
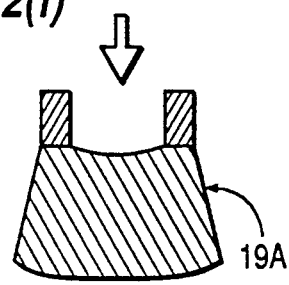
Figure 12C:
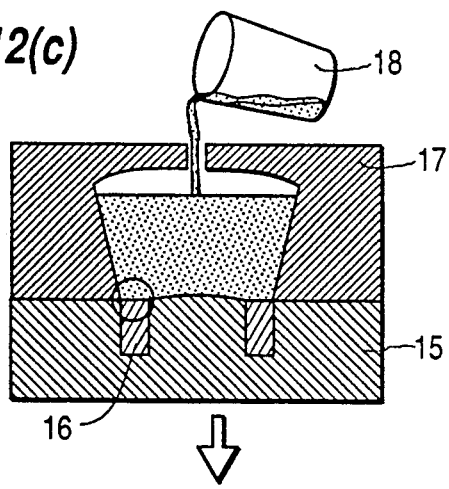
Figure 12D:
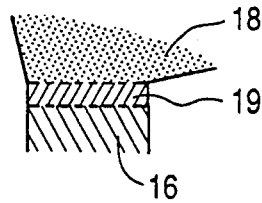
Figure 12D:
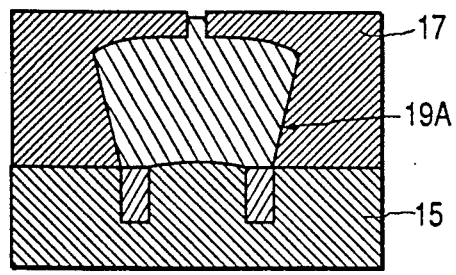

The third method is performed by the following steps with reference to FIGS. 12(a-f):

(1) pouring an aqueous solution 14 of 10% wt (more than 10% wt can be taken) PVA into a box 15 for molding a hardened PVA gel as shown in FIG. 12(a);

(2) gelling the aqueous solution 14 to a hardened PVA gel 16 by refrigerating the aqueous solution 14 to 0° C. (less than 0° C. is allowable) and thawing that to a room temperature as shown in FIG. 12(b), and repeating this refrigeration and thawing cycle four times (more than once is allowable);

(3) putting a box 17 for molding the usual PVA gel on the box 15 and pouring an aqueous solution 18 of 10% wt (less than 10% wt can be taken) PVA heated up to more than 80° C. into the box 17, resulting in partially melting the hardened PVA 16 near the interface between the hardened PVA gel 16 and the poured hot solution 18 as shown by reference numeral 19 in FIG. 12(c');

(4) refrigerating the both materials in the boxes 15 and 17 to 0° C. (less than 0° C. is allowable) and thawing them to a room temperature as shown in FIG. 12(d), producing a gelled material 19A, so that totally, five cycles of refrigeration and thawing have been done to the hardened PVA gel and one cycle has been done to the usual PVA gel; and (5) taking out the gelled material 19A consisting of a hardened part and a usual part from the boxed 15 and 17 as shown in FIG. 12(e) and cutting out a protruded part of material 19A as shown in FIG. 12(f).

A method of fabricating the acoustic coupler using the gelled material as explained in reference to FIG. 5 will be explained in accordance with the following steps in reference to FIGS. 13(a,b,c and d): (In this embodiment however, an illustrative example using the PVA gel as the gelled material is disclosed.)

Figure 13A:
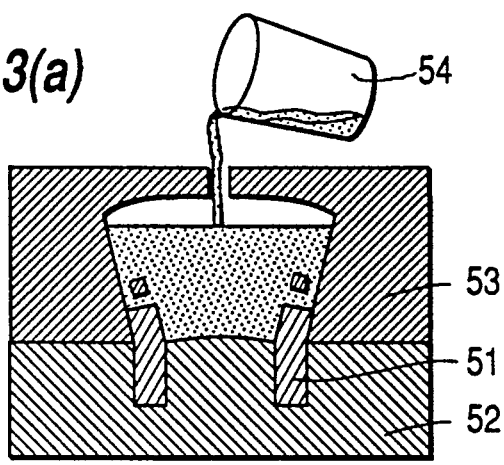
FIGS. 13(a) through (d) are schematic cross-sectional views illustrating steps of a method for fabricating an acoustic coupler consisting of a body made of the PVA gel and a combiner buried in the body.
Figure 13B:
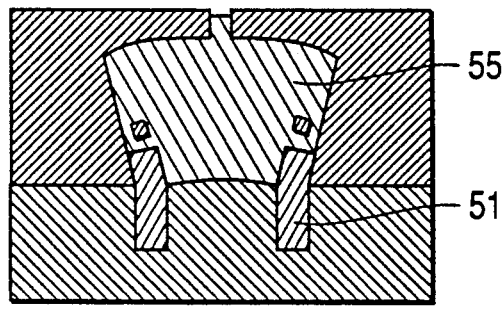
Figure 13C:
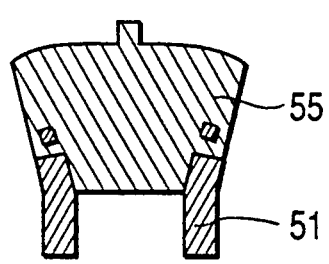
Figure 13D:
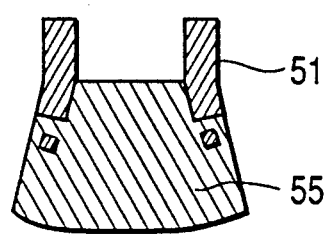

(1) previously providing a combiner 51 same as the combiner 42 in FIG. 5 and putting the combiner 51 in a box 52. As explained with reference to FIG. 5, the combiner 51 is made of an elastic material such as silicon rubber, plastic or a hardened PVA gel and has a plurality of holes to increase friction between the combiner 51 and the gelled material, putting another box 53 for molding a usual gelled material on the box 51, and pouring an aqueous solution 54 of 10% wt PVA into the box as shown in FIG. 13(a);

(2) refrigerating the solution 54° to −20° C. and thawing it to a room temperature twice for gelling the aqueous solution 54 to a usual PVA gel 55 including the combiner 51, resulting in burying the combiner 51 into the usual PVA gel 55 so that they are mechanically tightly connected as shown in FIG. 13(b); and (3) taking out the usual PVA gel 55 from the boxes 55 and 51 with the combiner 51 as shown in FIG. 13(c), and cutting a protruded part off as shown in FIG. 13(d).

When the general gelled material is used as the acoustic coupler shown in FIG. 5, the material such as silicon gel or paraffin gel is used in the same way as in FIGS. 13(a) through (d). However, a proper hardening agent is used for gelling the material which buys the combiner.

As stated in reference to FIGS. 17 and 18, the gelled material tends to dry up. Therefore, before combining the acoustic coupler of the gelled material with the ultrasound probe, it is better to sink the acoustic coupler in a liquid, such as water containing an antiseptic agent, stored in a container, for preserving the gelled material of the acoustic coupler. If such container is prepared, it will be better to make the container have a mechanism that the acoustic coupler in the liquid, which will be explained as "water" hereinafter for simplicity, can be combined with the ultrasound probe by simply pushing the probe into the container. This is achieved by the present invention as will be disclosed in the following embodiment in reference to FIGS. 14(a) and (b), 15(a) and (b) and 16(a) through (d). In this embodiment, inventions about not only the container but also acoustic couplers suitable for being stocked in the container will be disclosed.

Figure 14A:
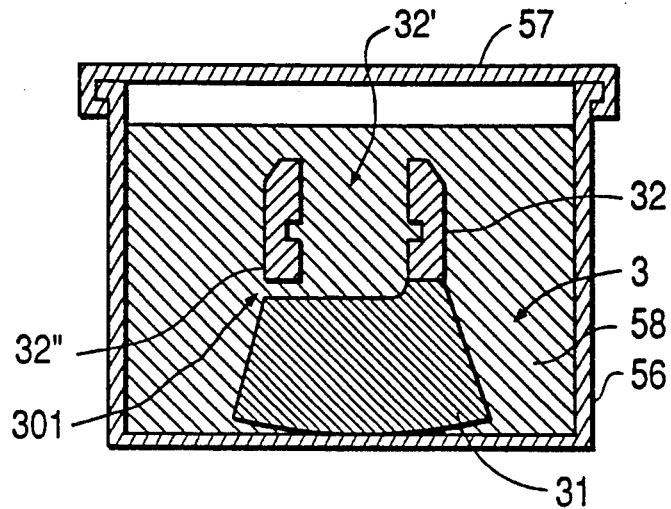
FIG. 14(a) is a schematic cross-sectional view illustrating an acoustic coupler stored in a container with water.
Figure 14B:
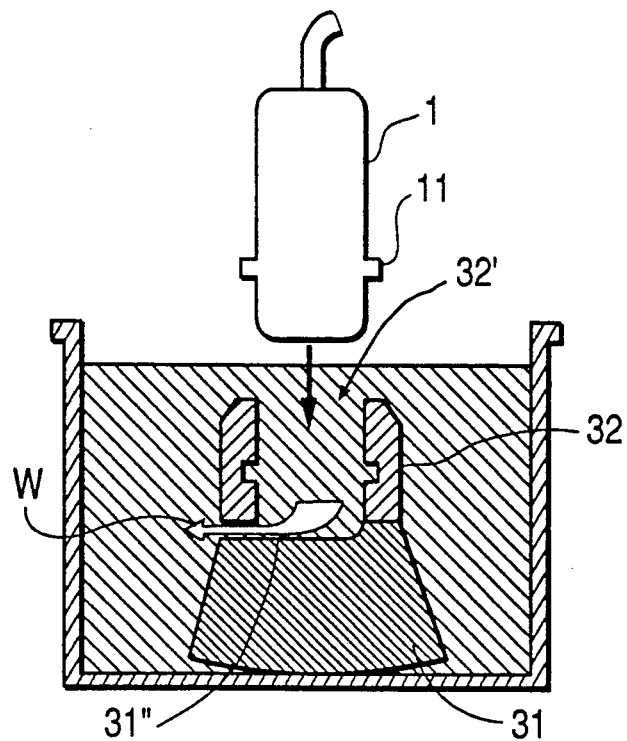
FIG. 14(b) is a schematic cross-sectional view illustrating that an ultrasound probe and the coupler can be stored in the container with water.

FIGS. 14(4) and 14(b) are cross-sectional views each illustrating a container 56 with a lid 57, in which water 58 is stored and the acoustic coupler 3 is stocked or stored in the water 58. The coupler 3 is same as the coupler 3 explained in reference to FIG. 6 except that the coupler 3 in FIG. 14(a) adds a hole 301. In FIGS. 14(a) and 14(b), the same reference numerals as used in FIG. 6 designate the same unit or part. When the probe 1 is pushed in the container 56 as shown in FIG. 14(b), the inlet mechanism 32' surrounded by the part 32 made of the hardened PVA gel of the coupler 3 is opened by the pushed probe 1 so that the end of the probe 1 is fitted to the upper surface 31" of the part 31 made of the usual PVA gel 31 of the coupler 3 and the ring 11 of probe 1 is slid in the ditch 32" or groove provided inside of the part 32. In this case the hole 301 operates so that the probe 1 is easily pushed into the inlet mechanism 32' because the water having been in the inlet mechanism 321 flows out through the hole 301 as shown by reference symbol W in FIG. 14(b). After pushing the probe 1 into the inlet mechanism 32' of the coupler 3, the probe 1 can be lifted up with the coupler 3.

Figure 15A:
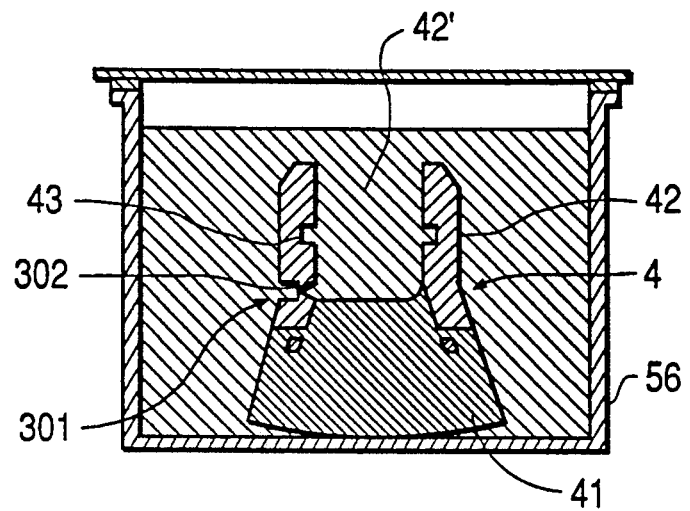
FIG. 15(a) is a schematic cross-sectional view illustrating another acoustic coupler stored in a container with water.
Figure 15B:
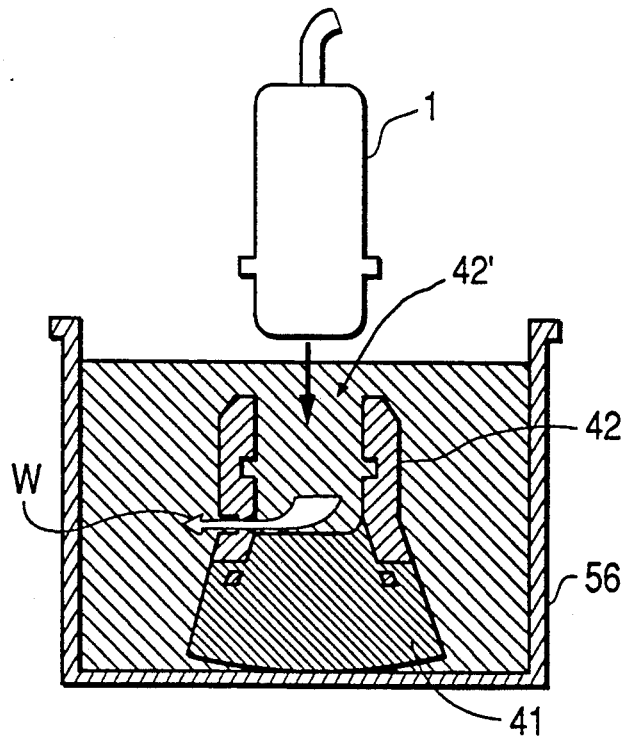
FIG. 15(b) is a schematic cross-sectional view illustrating that an ultrasound probe and coupler can be stored in the container with water.
Figure 16A:
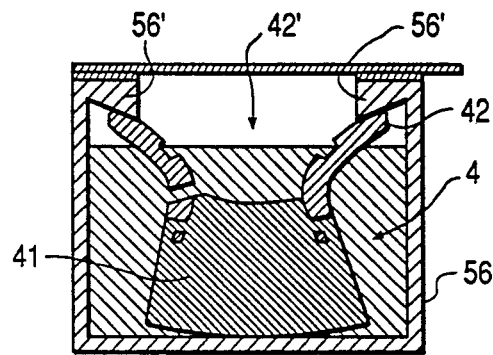
FIGS. 16(a) through (d) are schematic cross-sectional views illustrating the function of opening means provided with a container for storing an acoustic coupler.
Figure 16B:
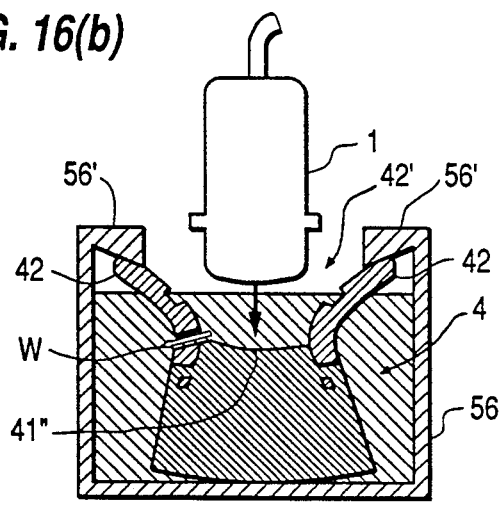
Figure 16D:
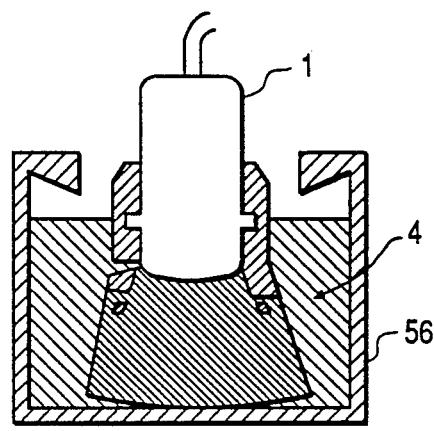
Figure 16C:
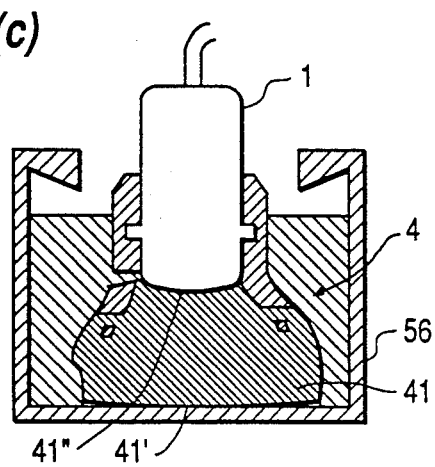

Another embodiment shown in FIGS. 15(a) and 15(b) is the same as the embodiment explained with reference to FIGS. 14(a) and 14(b) except that the acoustic coupler stocked in the container 56 is same as the acoustic coupler 4 in FIG. 5. In FIGS. 15(a) and 15(b), the same reference numerals as used in FIGS. 14(a,b) and FIG. 5 refer to the same unit or part. The differences from FIGS. 14(a,b) is that a valve 302 is provided for the hole 301. The valve 302 is to prevent water existing outside of the coupler 4 running back to the inlet mechanism 42'. The difference from FIG. 5 is that a ditch 43 or groove for accepting the ring 11 of the probe 1 is provided at the inside of the inlet mechanism 42'.

Still another embodiment shown in FIGS. 16(a,b,c and d) is the same as the embodiment explained in reference to FIGS. 15(a and b) except that an opening mechanism 56' for opening the inlet mechanism 42' of the probe 4 is provided in the container 56. In FIGS. 16(a)-(d), the same reference numerals as used in FIGS. 15(a) and (b) designate the same unit or part. After the coupler 4 is put in the container 56, the inlet mechanism 42' is opened by pushing the coupler toward the bottom of the container 56 and opening the inlet mechanism 42'. The inlet mechanism 42' kept in an opened state by hooking an end of the part 42 of the inlet mechanism 42' to the opening mechanism 56' of the container 56. The opened state of the inlet mechanism 42' of the coupler 4 is maintained until the probe 1 is pushed into the inlet mechanism 42' because of elastic force of the parts 41 and 42 of the coupler 4 as shown in FIG. 16(a). This state is a stand-by state of waiting for the probe 1 to be pushed into the inlet mechanism 42'. When the probe 1 pushes the upper surface 41" of the coupler 4 as shown in FIG. 16(b), the part 41 is also pushed against the bottom of the container 56. As a result, the part 42 slips off the opening mechanism 56' and the part 42 holds the probe 1 as shown in FIG. 16(c). Then, the probe 1 can be lifted up together with the coupler 4 as shown in FIG. 16(d).

The acoustic couplers embodying the present invention are also used with an ultrasound probe for general acoustical inspection of a defective part in an object.

What is claimed is:

1. An acoustic coupler used with an ultrasound probe and placed between a surface of an object to be acoustically inspected and the ultrasound probe, said acoustic coupler comprising:

a body made of an acoustically transparent gelled material having a hardness and an elastically both capable of being partially varied, said body including an upper surface, provided on a part of the acoustically transparent gelled material and having a low hardness, for receiving the ultrasound probe;

inlet means provided around said upper surface, said inlet means being comprised of the acoustically transparent gelled material and having a higher hardness than the acoustically transparent material having a low hardness, for combining said body with the ultrasound probe by holding the ultrasound probe therein by elastic force due to the acoustically transparent gelled material having a higher hardness and elasticity, and allowing movement of the ultrasound probe with said body as well as removal of the ultrasound probe from said body;

a lower surface, provided on the part of the acoustically transparent gelled material having a low hardness, said lower surface being adapted to be applied to the surface of the object; and an acoustically transparent path provided between said upper surface and said lower surface by using the acoustically transparent gelled material having a low hardness.

2. An acoustic coupler according to claim 1, wherein the acoustically transparent gelled material is a poly vinyl alcohol gel.

3. An acoustic coupler according to claim 1, wherein said acoustic coupler further comprises stopper means fitted to the ultrasound probe for increasing friction between the ultrasound probe and said inlet means when the ultrasound probe is pushed into said inlet means, said stopper means being able to be removed from the ultrasound probe.

4. An acoustic coupler according to claim 3, wherein said inlet means comprises a catching means engaged with said stopper means for catching the ultrasound probe when the ultrasound probe is pushed into said inlet means.

5. An acoustic coupler according to claim 1, wherein said acoustic coupler further comprises a covering film for preventing water vapor in said acoustically transparent body from evaporating.

6. An acoustic coupler according to claim 1 further comprising stopper means fitted to the probe for increasing friction between the probe and said inlet means when the probe is pushed in said inlet means, said stopper means being able to be removed from the probe.

7. An acoustic coupler according to claim 1 further comprising a covering film for preventing water vapor in said body from evaporating.

8. An acoustic coupler according to claim 1, wherein said inlet means includes a hole in a wall thereof for allowing water in said inlet means to flow out therefrom when said acoustic coupler is stored in water and the ultrasound probe is pushed into said inlet means.

9. An acoustic coupler according to claim 8, wherein said hole includes a valve for allowing water in said inlet means to flow out therefrom while preventing water existing outside of said body from flowing into said inlet means.

10. An acoustic coupler according to claim 1, wherein said lower surface of said body is concave.

11. An acoustic coupler used with an ultrasound probe and placed between a surface of an object to be acoustically inspected and the ultrasound probe, said acoustic coupler comprising:
- an acoustically transparent body made of an acoustically transparent gelled material, said acoustically transparent body including
  - an upper surface to be fitted to the ultrasound probe;
  - a lower surface to be applied to the surface of the object; and
  - an acoustically transparent path provided between said upper surface and said lower surface;
- combining means made of an elastic material, for combining said acoustically transparent body with the ultrasound probe whereby the ultrasound probe is fitted to said upper surface by an elastic force of the elastic material, said combining means allowing said acoustically transparent body to move with the ultrasound probe and removal of the ultrasound probe from said acoustically transparent body, said combining means being mounted to said acoustically transparent body around said upper surface; and
- a covering film for preventing water vapor in said acoustically transparent body from evaporating.

12. An acoustic coupler used with an ultrasound probe and placed between a surface of an object to be acoustically inspected and the ultrasound probe, said acoustic coupler comprising:
- an acoustically transparent body made of an acoustically transparent gelled material, said acoustically transparent body including
  - an upper surface to be fitted to the ultrasound probe;
  - a lower surface to be applied to the surface of the object; and
  - an acoustically transparent path provided between said upper surface and said lower surface; and
- combining means made of an elastic material, for combining said acoustically transparent body with the ultrasound probe whereby the ultrasound probe is fitted to said upper surface by an elastic force of the elastic material, said combining means allowing said acoustically transparent body to move with the ultrasound probe and removal of the ultrasound probe from said acoustically transparent body, said combining means being mounted to said acoustically transparent body around said upper surface; and
- wherein said combining means includes a hole for allowing water in said combining means to flow out therefrom when said acoustic coupler is stored in water and the ultrasound probe is pushed into said combining means.

13. An acoustic coupler according to claim 12, wherein said hole includes a valve for allowing water in said combining means to flow out therefrom while preventing water existing outside of said acoustically transparent body from flowing into said combining means.

14. An acoustic coupler used with an ultrasound probe and placed between a surface of an object to be acoustically inspected and the ultrasound probe, said acoustic coupler comprising:
- an acoustically transparent body made of an acoustically transparent gelled material, said acoustically transparent body including
  - an upper surface to be fitted to the ultrasound probe;
  - a lower surface to be applied to the surface of the object; and
  - an acoustically transparent path provided between said upper surface and said lower surface; and
- combining means made of an elastic material, for combining said acoustically transparent body with the ultrasound probe whereby the ultrasound probe is fitted to said upper surface by an elastic force of the elastic material, said combining means allowing said acoustically transparent body to move with the ultrasound probe and removal of the ultrasound probe from said acoustically transparent body, said combining means being mounted to said acoustically transparent body around said upper surface; and
- wherein said combining means is a stand-up collar, said stand-up collar being partially buried in said acoustically transparent body.

15. An acoustic coupler according to claim 14, wherein said stand-up collar includes a plurality of holes in a portion of said stand-up collar partially buried for increasing the elastic force holding said stand-up collar to said acoustically transparent body.

16. An acoustic coupler according to claim 14, wherein said lower surface of said acoustically transparent body is concave.

17. An acoustic coupler for an ultrasonic probe, comprising:
- an upper portion, formed from an acoustically transparent material having a first hardness, said upper portion including an ultrasonic probe holding means for holding the ultrasonic probe to said acoustic coupler using elastic forces produced from the acoustically transparent material having the first hardness; and
- a lower portion, coupled to said upper portion and formed from acoustically transparent material having a second hardness, the first hardness of said upper portion being greater than the second hardness of said lower portion; and
- wherein the ultrasonic probe includes a ring, and said ultrasonic probe holding means includes a groove for receiving the ring of the ultrasonic probe when the ultrasonic probe is held to said acoustic coupler, to increase the elastic forces holding the ultrasonic probe.

18. An acoustic coupler according to claim 17, wherein the ultrasonic probe includes a probe combiner, and
said ultrasonic probe receiving means further includes an exterior notch for receiving the probe combiner.

19. An acoustic coupler for allowing an ultrasonic probe to incline from a vertical position when attached to said acoustic coupler, said acoustic coupler comprising:
a lower portion of an acoustically transparent gelled material; and
an upper portion of elastic material coupled to said lower portion, said upper portion including
ultrasonic probe holding means for holding the ultrasonic probe to said acoustic coupler using elastic forces produced by the elastic material; and
lower portion holding means for flexibly holding said upper portion to said lower portion while allowing the ultrasonic probe to adjustably incline with respect to said acoustically transparent gelled material while attached to said acoustic coupler; and
wherein said lower portion of acoustically transparent gelled material has a top surface and a bottom surface, and
said lower portion holding means comprises a flexible case with a greater thickness near the top surface than at the bottom surface of said lower portion.

* * * * *

UNITED STATES PATENT AND TRADEMARK OFFICE
CERTIFICATE OF CORRECTION

PATENT NO. : 5,265,614
DATED : November 30, 1993
INVENTOR(S) : Kenichi HAYAKAWA et al.

It is certified that error appears in the above-identified patent and that said Letters Patent is hereby corrected as shown below:

Col. 2, line 10, after "which" insert --is--;
    line 37, after "probe" insert --and--; and
    line 58, delete "mainly".
    line 35, after "MACHIDA" insert --on--.

Col. 3, line 38, after "an" insert --ultrasound probe and directly applied to the surface of the--;
    line 38, change "a" to --the--; and
    line 57, after "freely" delete --,--.

Col. 6, line 17, change "23'; further" to --23'. Further,--
    line 18, delete "and";
    line 23, after "art" delete "," and insert --. The--;
    line 42, change "separate" to --separated--;
    line 47, delete "therefor elasticity-- and insert --(that is, elasticity)--; and
    line 54, insert --()-- around "PVA gel having a large or high hardness".

Col. 7, line 21, change "11" to --1'--;
    line 52, change "be be" to --to be--; and
    line 58, after "together" insert --with the--.

UNITED STATES PATENT AND TRADEMARK OFFICE
CERTIFICATE OF CORRECTION

PATENT NO. : 5,265,614
DATED : November 30, 1993
INVENTOR(S) : Kenichi HAYAKAWA et al.

It is certified that error appears in the above-identified patent and that said Letters Patent is hereby corrected as shown below:

Col. 8, line 11, after "combiner" insert --11'--;
      line 18, after "PVA" insert --gel 31--;
      line 39, change "FIG." to --FIGS.--;
      line 40, change "numeral" to --numerals--;
      line 41, after "(a)" insert --,--;
      line 55, after "A" insert --which is designated--;
      line 61, change "intends" to --tends--; and
      line 63, change "use" to --used--.

Col. 9, line 21, after "C" delete ".";
      line 33, insert --()-- around "couplers' dimensions";
      line 40, insert --()-- around "hardened PVA gel";
      line 45, after "hardness" insert --)--; and
      line 49, change "N/M$^2$" to --N/m$^2$--.

Col. 10, line 4, change "+" to --°C--;
      line 9, change "materially" to --material--; and
      line 60, delete "54°" and insert --54--.

Col. 11, line 43, change "321" to --32'--; and
      line 53, change "differences" to --difference--.

UNITED STATES PATENT AND TRADEMARK OFFICE
CERTIFICATE OF CORRECTION

PATENT NO. : 5,265,614

DATED : November 30, 1993

INVENTOR(S) : Kenichi HAYAKAWA et al.

It is certified that error appears in the above-identified patent and that said Letters Patent is hereby corrected as shown below:

Col. 13, line 8, change "in" to --into--.

Signed and Sealed this

Twenty-fifth Day of October, 1994

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,265,614
DATED : November 30, 1993
INVENTOR(S) : Kenichi HAYAKAWA et al.

It is certified that error appears in the above-indentified patent and that said Letters Patent is hereby corrected as shown below:

Col. 2, line 10, after "which" insert --is--;
    line 37, after "probe" insert --and--; and
    line 58, delete "mainly".
    line 35, after "machida" insert --on--.

Col. 3, line 38, after "an" insert --ultrasound probe and directly applied to the surface of the--;
    line 38, change "a" to --the--; and
    line 57, after "freely" delete --,--.

Col. 6, lines 17, 18 change "23'; further" to --23 and further--;
    line 18, delete "and";
    line 23, after "art" delete "," and insert --. The--;
    line 42, change "separate" to --separated--;
    line 47, delete "therefor elasticity-- and insert --(that is, elasticity)--; and
    line 54, insert --()-- around "PVA gel having a large or high hardness".

Col. 7, line 21, change "11" to --1'--;
    line 52, change "be be" to --to be--; and
    line 58, after "together" insert --with the--.

UNITED STATES PATENT AND TRADEMARK OFFICE
CERTIFICATE OF CORRECTION

PATENT NO. : 5,265,614
DATED : November 30, 1993
INVENTOR(S) : Kenichi HAYAKAWA et al.

It is certified that error appears in the above-indentified patent and that said Letters Patent is hereby corrected as shown below:

Col. 8, line 11, after "combiner" insert --11'--;
       line 18, after "PVA" insert --gel 31--;
       line 39, change "FIG." to --FIGS.--;
       line 40, change "numeral" to --numerals--;
       line 41, after "(a)" insert --,--;
       line 55, after "A" insert --which is designated--;
       line 61, change "intends" to --tends--; and
       line 63, change "use" to --used--.

Col. 9, line 33, insert --()-- around "couplers' dimensions";
       line 40, insert --()-- around "hardened PVA gel";
       line 45, after "hardness" insert --)--; and
       line 49, change "N/M$^2$" to --N/m$^2$--.

Col. 10, line 4, change "+C" to --°C--;
       line 9, change "materially" to --material--; and
       line 60, delete "54°" and insert --54--.

Col. 11, line 43, change "321" to --32'--; and
       line 53, change "differences" to --difference--.

UNITED STATES PATENT AND TRADEMARK OFFICE
CERTIFICATE OF CORRECTION

PATENT NO. : 5,265,614
DATED : November 30, 1993
INVENTOR(S) : Kenichi HAYAKAWA et al.

It is certified that error appears in the above-indentified patent and that said Letters Patent is hereby corrected as shown below:

Col. 13, line 8, change "in" to --into--.

This certificate supersedes Certificate of Correction issued October 25, 1994.

Signed and Sealed this

Twenty-first Day of March, 1995

BRUCE LEHMAN

Attest:

Attesting Officer

Commissioner of Patents and Trademarks